(12) United States Patent
Kawanishi et al.

(10) Patent No.: US 7,493,802 B2
(45) Date of Patent: Feb. 24, 2009

(54) LIQUID TYPE IDENTIFICATION DEVICE

(75) Inventors: Toshiaki Kawanishi, Ageo (JP);
Takayuki Takahata, Ageo (JP); Kiyoshi Yamagishi, Ageo (JP)

(73) Assignee: Mitsui Mining & Smelting Co., Ltd., Tokyo (JP)

( * ) Notice: Subject to any disclaimer, the term of this patent is extended or adjusted under 35 U.S.C. 154(b) by 389 days.

(21) Appl. No.: 10/586,920

(22) PCT Filed: Jan. 25, 2005

(86) PCT No.: PCT/JP2005/000894
§ 371 (c)(1),
(2), (4) Date: Jul. 24, 2006

(87) PCT Pub. No.: WO2005/073700
PCT Pub. Date: Aug. 11, 2005

(65) Prior Publication Data
US 2007/0151331 A1    Jul. 5, 2007

(30) Foreign Application Priority Data
Jan. 30, 2004   (JP)   ............................. 2004-023645

(51) Int. Cl.
*G01N 25/00* (2006.01)
(52) U.S. Cl. .................................................. 73/61.76
(58) Field of Classification Search ................. 73/61.76
See application file for complete search history.

(56) References Cited
U.S. PATENT DOCUMENTS
2007/0237206 A1* 10/2007 Kubota et al. ............... 374/164

(Continued)

FOREIGN PATENT DOCUMENTS
JP   04-178550 A   6/1992

(Continued)

*Primary Examiner*—Hezron Williams
*Assistant Examiner*—Rodney T Frank
(74) *Attorney, Agent, or Firm*—Frommer Lawrence & Haug LLP; Ronald R. Santucci

(57) ABSTRACT

There is provided an identification device capable of accurately, rapidly, and easily identifying a hydrocarbon-based liquid and alcohol-based liquid. An identification sensor unit (2) is arranged to face a flow passage (20) of a liquid to be measured and includes a liquid type detection unit with indirect heating (21) having a heating body and a temperature-sensitive body, and a liquid temperature detecting unit (22) for detecting the temperature of the liquid to be measured. The identification device further includes an identification calculation unit for applying a single pulse voltage to the heating body of the liquid type detection unit (21) so as to generate heat and identifying the liquid to be measured according to an output of a liquid type detection circuit formed by the temperature-sensitive body of the liquid type detecting unit (21) and the liquid temperature detection unit. The identification calculation unit identifies the liquid to be measured according to a liquid-type-corresponding first voltage value corresponding to a difference between the initial temperature of the temperature-sensitive body when the heating body generates heat and a first temperature at the moment when the a first time has elapsed from the start of application of the single pulse and a liquid-type-corresponding second voltage value corresponding to a difference between the initial temperature of the temperature-sensitive body and a second temperature at the moment when a second time longer than the first time has elapsed from the start of application of the single pulse.

24 Claims, 11 Drawing Sheets

U.S. PATENT DOCUMENTS

2008/0066531 A1 * 3/2008 Kawanishi et al. ......... 73/61.76

FOREIGN PATENT DOCUMENTS

| JP | 05-033712 Y2 | 8/1993 |
| JP | 11-153561 A | 6/1999 |
| JP | 11-237356 A | 8/1999 |
| JP | 2001-004422 A | 1/2001 |
| JP | 2004-125465 A | 4/2004 |
| JP | 2004-101385 A | 4/2006 |

* cited by examiner

LIQUID TYPE IDENTIFICATION DEVICE

This application is a 371 of PCT/JP2005/000894 filed on Jan. 25, 2005, published on Aug. 11, 2005 under publication number WO 2005/073700A1 which claims priority benefits from Japanese Patent Application Number 2004-023645 filed Jan. 30, 2004.

TECHNICAL FIELD

The present invention relates to a liquid type identification device which uses thermal properties of liquid to identify the liquid type.

BACKGROUND ART

In general, gasoline or gas oil is used in an internal-combustion engine of a car. Such a fuel is a mixture of various hydrocarbons and other materials. In the light of concerns about a future reduction in the output of fossil fuels and in the light of a strong request for a reduction in emission of carbon dioxide in the fight against global warming, it is currently being studied that alcohol (e.g., ethanol or methanol) which is a plant-derived fuel is mixed in the gasoline for the fuel of an internal-combustion engine.

The material composition of such a fuel is determined based on the material composition and distillation condition of crude oil which is the raw material of gasoline or gas oil, addition amount of alcohol, and the like. Accordingly, properties concerning combustion of such a fuel differ depending on the material composition thereof. Therefore, even if a combustion condition (air-fuel ratio or amount of fuel injection per unit time) on the internal-combustion engine side is optimally set on the assumption of combustion of one fuel having a given material composition, the combustion condition is not optimal for another fuel in some cases.

In order to increase the output efficiency of the internal-combustion engine to reduce fuel consumption and, at the same time, to reduce the amount of hydrocarbon (HC) or carbon monoxide (CO) which is a product of incomplete combustion contained in exhaust gas, air needs to be mixed with a fuel to be supplied to the internal-combustion engine at an ideal ratio (i.e., air-fuel ratio is optimized) for combustion depending on the kind of the fuel.

In order to make the material composition of a fuel constant and thereby prevent the optimal combustion condition from being changed, it is now proposed that one material or a mixture of, at most, two materials selected from hydrocarbons (such as pentane, cyclohexane, octane) which are components of the fossil fuel and alcohols (such as methanol, and ethanol) are used as a fuel. This type of fuel roughly includes a hydrocarbon-based fuel and alcohol-based fuel.

When such various types of fuels are sold in the same manner in service station and the like, it becomes likely that a fuel tank in a car is erroneously replenished with a fuel different from a predetermined one. If such occurs, the engine output efficiency may decrease extremely. Such a situation must be avoided.

Therefore, it is desirable that a car is to be provided with a mechanism capable of detecting the type of a fuel to be supplied from its fuel tank to internal-combustion engine and checking whether the supplied fuel is a predetermined one.

Further, in the case where the detected type of the fuel is similar to a predetermined one, it is desirable to optimize the combustion condition of the internal combustion engine depending on the detected type. That is, it is desirable to identify the type of the fuel to be actually supplied to the internal combustion engine and appropriately set the combustion condition of the internal combustion engine based on the identification result and thereby realize a suitable combustion state (i.e., combustion state that increases the output torque of the internal-combustion engine while reducing the amount of products of incomplete combustion contained in exhaust gas) in accordance with the type of the fuel to be actually used in the combustion.

Since the combustion properties and physical properties of the hydrocarbon-based fuel differ from those of the alcohol-based fuel, it is important to firstly determine a group, i.e. hydrocarbon-based fuel or alcohol-based fuel, to which a liquid (fuel) to be measured belongs. It is preferable, after the determination, to identify in more detail the type of the hydrocarbon-based fuel or that of the alcohol-based fuel.

A method of identifying the type of a fluid including a liquid is disclosed in, e.g., JP-A-11-153561 (Patent Document 1). This method comprises supplying an electric current to a heating body so as to generate heat to thereby heat a temperature-sensitive body, giving thermal effect to the heat transfer from the heating body to temperature-sensitive body using a fluid to be identified, and identifying the type of the fluid to be identified based on an electrical output value corresponding to the impedance of the temperature-sensitive body. In this fluid identification method, a current is periodically supplied to the heating body.

Patent Document 1: JP-A-11-153561 (paragraphs [0042] to [0049])

DISCLOSURE OF THE INVENTION

Problems to be Solved by the Invention

However, although the fluid identification method disclosed in the Patent Document 1 can identify a distinction among fluids such as water, air, and oil, among which there is a significant difference in physical nature using representative values, it cannot satisfactorily make a distinction between the above-mentioned hydrocarbon-based liquid and alcohol-based liquid accurately and rapidly.

In view of the above present situation, an object of the present invention is to provide an identification device capable of accurately, rapidly, and easily identifying a hydrocarbon-based liquid and alcohol-based liquid particularly capable of being used as fuel.

Another object of the present invention is to provide an identification device capable of accurately, rapidly, and easily identify the type of the hydrocarbon-based liquid or alcohol-based liquid.

Means for Solving the Problem

To attain the above objects, according to the present invention, there is provided a liquid type identification device which identifies a liquid to be measured belonging to a hydrocarbon-based liquid or an alcohol-based liquid, comprising:

an identification sensor unit which faces a flow passage of the liquid to be measured, the identification sensor unit including a liquid type detection unit with indirect heating which includes a heating body and a temperature-sensitive body and including a liquid temperature detection unit which detects the temperature of the liquid to be measured; and an identification calculation unit which applies a single pulse voltage to the heating body of the liquid type detection unit with indirect heating so as to generate heat and identifies the liquid to be measured according to an output of a liquid type detection circuit formed by the temperature-sensitive body of the liquid type detection unit with indirect heating and the liquid temperature detection unit, wherein the identification calculation unit identifies the liquid to be measured according to a liquid-type-corresponding first voltage value and a liquid-type-corresponding second voltage value, the liquid-type-corresponding first voltage value corresponding to a difference between the initial temperature of the temperature-sensitive body and a first temperature thereof at a time point when a first time period has elapsed from the start of application of the single pulse, the liquid-type-corresponding second voltage value corresponding to a difference between the initial temperature of the temperature-sensitive body and a second temperature thereof at a time point when a second time period longer than the first time period has elapsed from the start of the application of the single pulse.

In an aspect of the present invention, the second time period is the application time of the single pulse. In an aspect of the present invention, the first time period is ½ or less of the application time of the single pulse. In an aspect of the present invention, the first time period is 0.5 to 1.5 seconds. In an aspect of the present invention, the application time of the single pulse is 3 to 10 seconds.

In an aspect of the present invention, an averaged initial voltage value obtained by sampling the initial voltage before the start of the single pulse application to the heating body for a predetermined number of times and averaging the sampled values is used as a voltage value corresponding to the initial temperature of the temperature-sensitive body; an averaged first voltage value obtained by sampling a first voltage at a time point when the first time period has elapsed from the start of the single pulse application to the heating body for a predetermined number of times and averaging the sampled values is used as a voltage value corresponding to the first temperature of the temperature-sensitive body; an averaged second voltage value obtained by sampling a second voltage at a time point when the second time period has elapsed from the start of the single pulse application to the heating body for a predetermined number of times and averaging the sampled values is used as a voltage value corresponding to the second temperature of the temperature-sensitive body; a difference between the averaged first voltage value and averaged initial voltage value is used as the liquid-type-corresponding first voltage value; and a difference between the averaged second voltage value and averaged initial voltage value is used as the liquid-type-corresponding second voltage value.

In an aspect of the present invention, a liquid temperature-corresponding output value corresponding to the temperature of the liquid to be measured is input to the identification calculation unit from the liquid temperature detection unit, and the identification calculation unit uses a calibration curve indicating a relationship between the liquid temperatures and liquid-type-corresponding first voltage values of a plurality of types of known reference liquids to be measured to determine whether the liquid to be measured is the hydrocarbon-based liquid or alcohol-based liquid based on the liquid temperature-corresponding output value and liquid-type-corresponding first voltage value obtained for the liquid to be measured. In an aspect of the present invention, a liquid temperature-corresponding output value corresponding to the temperature of the liquid to be measured is input to the identification calculation unit from the liquid temperature detection unit, and the identification calculation unit uses a calibration curve which is created respectively for the hydrocarbon-based liquid and alcohol-based liquid and which indicates a relationship between the liquid temperatures and liquid-type-corresponding second voltage values of a plurality of types of known reference liquids to be measured belonging respectively to the hydrocarbon-based liquid and alcohol-based liquid to identify the liquid to be measured based on the liquid temperature-corresponding output value, liquid-type-corresponding second voltage value and the determination result obtained for the liquid to be measured.

In an aspect of the present invention, the identification calculation unit includes a microcomputer. In an aspect of the present invention, n both the liquid type detection unit with indirect heating and liquid temperature detection unit respectively include a heat transfer member for liquid type detection unit and a heat transfer member for liquid temperature detection unit, which are used for heat exchange with the liquid to be measured.

Effect of the Invention

According to the present invention, a single pulse voltage is applied to the heating body of the liquid type detection unit with indirect heating so as to generate heat and, based on an output of a liquid type detection circuit, the identification calculation unit identifies the liquid to be measured belonging to the hydrocarbon-based liquid or alcohol-based liquid by using the liquid-type-corresponding first voltage value and liquid-type-corresponding second voltage value obtained when the heating body is heated. With the above operation, it is possible to rapidly and easily identify the liquid to be measured.

In particular, an averaged initial voltage value is used as a voltage value corresponding to the initial temperature of the temperature-sensitive body, an averaged first voltage value is used as a voltage value corresponding to a first temperature of the temperature-sensitive body, an averaged second voltage value is used as a voltage value corresponding to a second temperature of the temperature-sensitive body, a difference between the averaged first voltage value and averaged initial voltage value is used as the liquid-type-corresponding first voltage value, and a difference between the averaged second voltage value and averaged initial voltage value is used as the liquid-type-corresponding second voltage value. With the above configuration, a stable identification can be achieved.

By determining whether the liquid to be measured is the hydrocarbon-based or alcohol-based liquid using a first calibration curve indicating a relationship between the liquid temperature and liquid-type-corresponding first voltage value based on the liquid temperature-corresponding output value and liquid-type-corresponding first voltage value of the liquid to be measured, and by identifying the liquid to be measured using a second calibration curve indicating a relationship between the liquid temperature and liquid-type-corresponding second voltage value obtained respectively for the hydrocarbon-based liquid and alcohol-based liquid based on the liquid temperature-corresponding output value, liquid-type-corresponding second voltage value, and result of the above determination obtained for the liquid to be measured, more accurate identification of the liquid to be measured can be achieved.

BEST MODE FOR CARRYING OUT THE INVENTION

An embodiment of the present invention will be described below with reference to the accompanying drawings.

Figure 1:
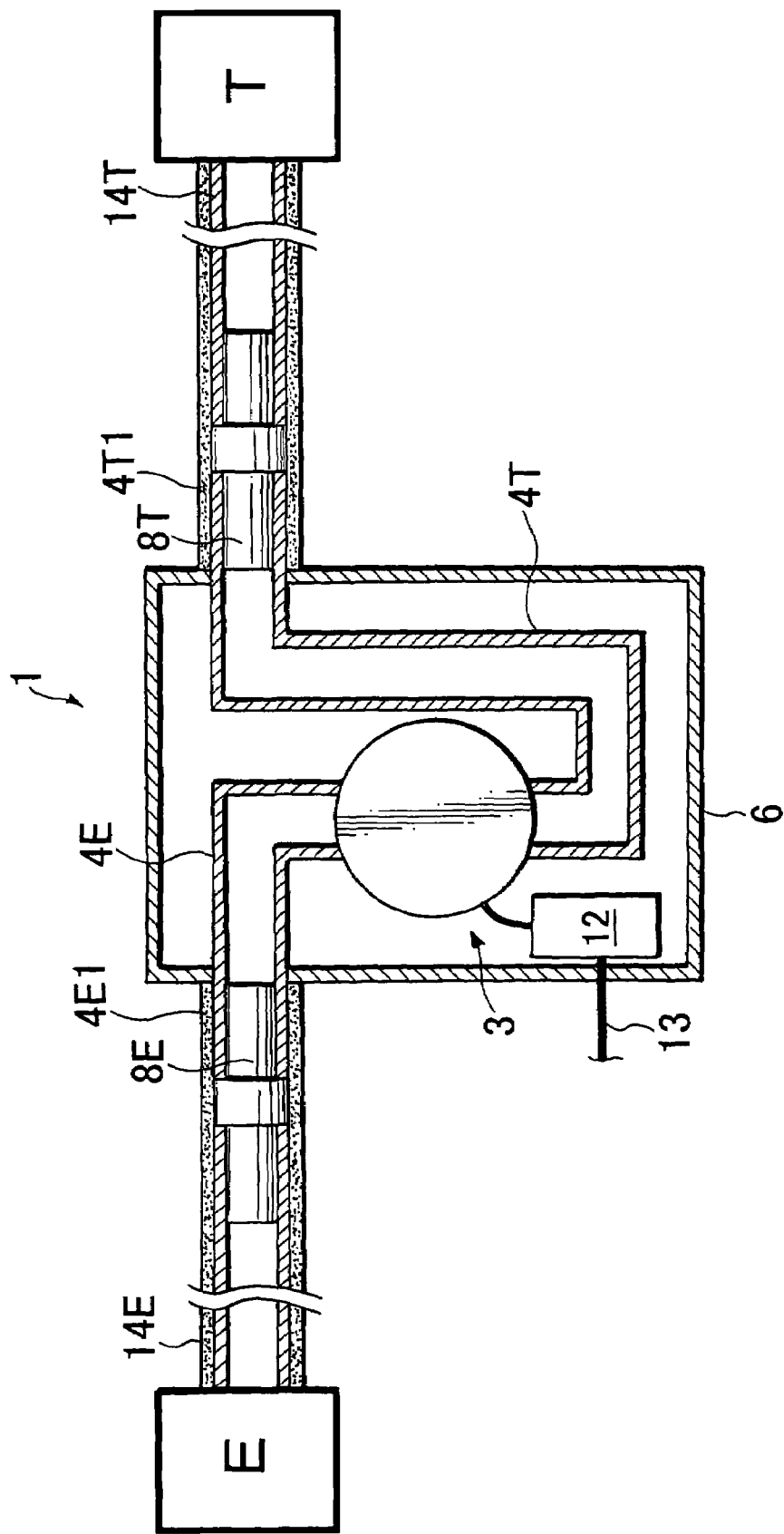
FIG. 1 is a schematic configuration view showing a use state of an embodiment of a liquid type identification device according to the present invention.
Figure 2:
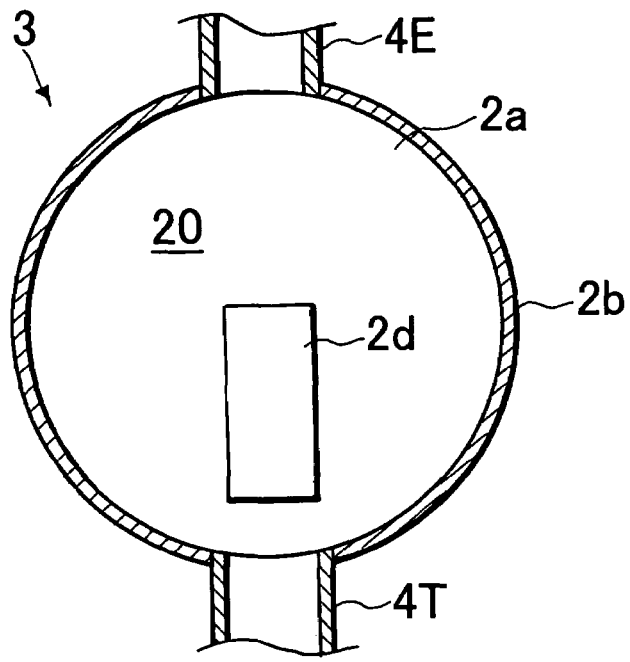
FIG. 2 is a cross-sectional view of a portion of the device of FIG. 1.
Figure 3:
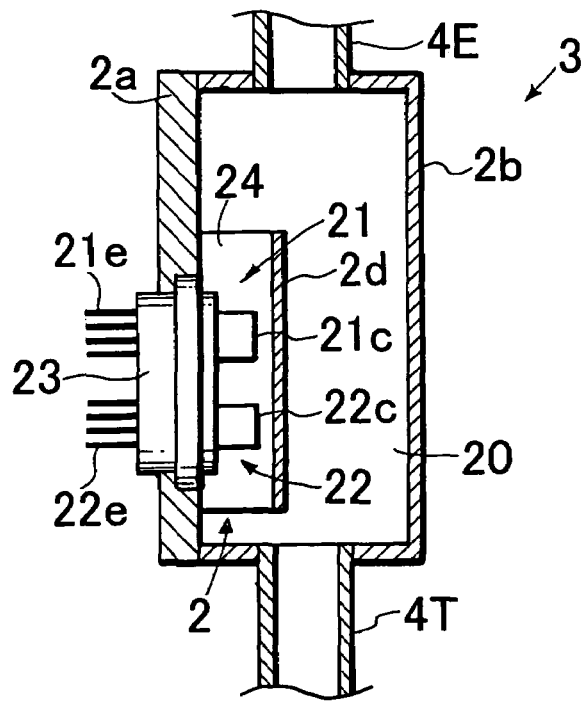
FIG. 3 is a cross-sectional view of a portion of the device of FIG. 1.
Figure 4:
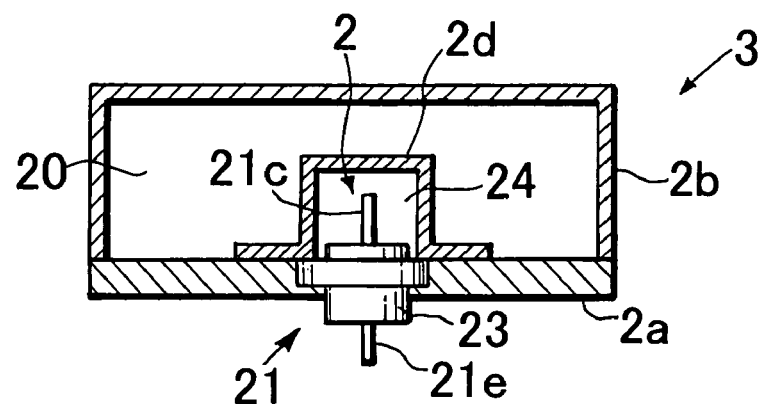
FIG. 4 is a cross-sectional view of a portion of the device of FIG. 1.

FIG. 1 is a schematic configuration view showing a use state of an embodiment of a liquid type identification device according to the present invention. FIGS. 2 to 4 are cross-sectional views of the respective portions of the device. In the present embodiment, a supply passage of a liquid (fuel) to be measured supplies the liquid to be measured from a tank of the liquid to an internal-combustion engine. However, the supply passage of liquid to be measured of the present invention is not limited to this, but it may be a passage that supplies a liquid to be measured from a tank to a tank truck or from a large-sized tank to a small-sized tank.

As shown in FIG. 1, a liquid type identification device 1 for identifying the type of a liquid to be measured is provided in the middle of a supply passage for supplying the liquid to be measured from a tank T for liquid to be measured to an internal-combustion engine E. The identification device 1 includes a measurement unit 3, a first flow passage 4T whose one end is connected to a tank side potion (piping) 14T which is located on the upstream side of the liquid supply passage by a pipe joint 8T, and a second flow passage 4E whose one end is connected to an internal-combustion engine side potion (piping) 14E which is located on the downstream side of the liquid supply passage by a pipe joint 8E. The measurement unit 3 has a flow passage 20 of liquid to be measured formed by a case base plate 2a and a case cover 2b. One end (lower end, in FIGS. 1 to 3) of the flow passage 20 is connected to the other end of the first flow passage 4T and the other end (upper end, in FIGS. 1 to 3) of the flow passage 20 is connected to the other end of the second flow passage 4E.

The identification device according the present embodiment includes a housing 6 that contains the measurement unit 3, a potion of the first flow passage 4T (i.e., a potion other than the end portion connected to the tank side portion 14T of the liquid supply passage, as shown in FIG. 1, and a portion of the second flow passage 4E (i.e., a potion other than the end portion connected to the engine side portion 14E of the liquid supply passage, as shown in FIG. 1). The portion of the first flow passage 4T outside the housing 6 (i.e., end portion connected to the tank side portion 14T of the liquid supply passage) is covered by a heat insulation cover 4T1 and the portion of the second flow passage 4E outside the housing 6 (i.e., end portion connected to the engine side portion 14E of the liquid supply passage) is covered by a heat insulation cover 4E1.

A circuit board 12 that constitutes a liquid type detection circuit to be described later is disposed in the housing 6. A microcomputer that constitutes an identification calculation unit to be described later is mounted on the circuit board 12. In addition, a wiring 13 for communication between the circuit board 12 and an external device is connected to the circuit board 12.

A heat insulation material fills the internal space of the housing 6 (i.e., a portion other than the measurement unit 3, first flow passage 4T, second flow passage 4E, circuit board 12, etc.). As the heat insulation material and the above-mentioned heat insulation covers 4T1 and 4E1, for example, those made of a rubber or foamed plastic can be used. Thus, even if the first flow passage 4T and second flow passage 4E are formed of metal, the existence of the heat insulation covers 4T1 and 4T1, housing 6, and the heat insulation material reduces the influence of the external temperature on the measurement unit 3, increasing identification accuracy. In the case where the housing 6 is not provided, it is preferable to cover the entire area of the first and second flow passages 4T and 4E with the heat insulation material.

Figure 5:
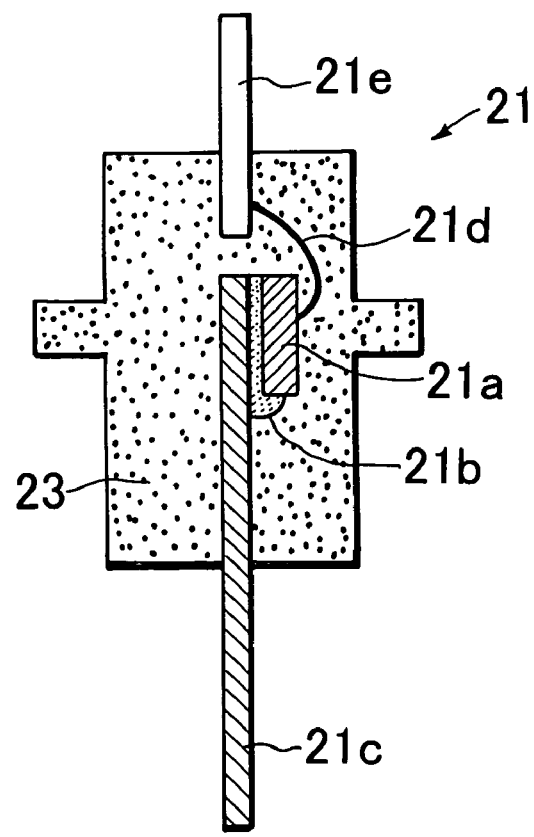
FIG. 5 is a cross-sectional view of an indirect heating type liquid type detection unit.

The measurement unit 3 further has an identification sensor unit 2 that faces the flow passage 20 of liquid to be measured. The identification sensor unit 2 has a liquid type detection unit with indirect heating 21 including a heating body and a temperature-sensitive body and a liquid temperature detection unit 22 for detecting the temperature of the liquid to be measured. The liquid type detection unit with indirect heating 21 and liquid temperature detection unit 22 are vertically spaced apart from each other by a predetermined distance. FIG. 5 shows a cross-sectional view of the liquid type detection unit with indirect heating 21.

As shown in the drawings, the liquid type detection unit with indirect heating 21 and liquid temperature detection unit 22 are integrated with each other by a molded resin 23. As shown in FIG. 5, the liquid type detection unit with indirect heating 21 has a thin film chip 21a including a heating body and a temperature-sensitive body, a metal fin 21c serving as a heat transfer member for liquid temperature detection unit jointed to the thin film chip by a jointing material 21b, and an external electrode terminal 21e which is electrically connected to electrodes of the heating body and temperature-sensitive body of the thin film chip by a bonding wire 21d. The liquid temperature detection unit 22, which has a same configuration as the liquid type detection unit with indirect heating 21, has a metal fin 22c serving as a heat transfer member for liquid temperature detection unit and an external electrode terminal 22e.

Figure 6:
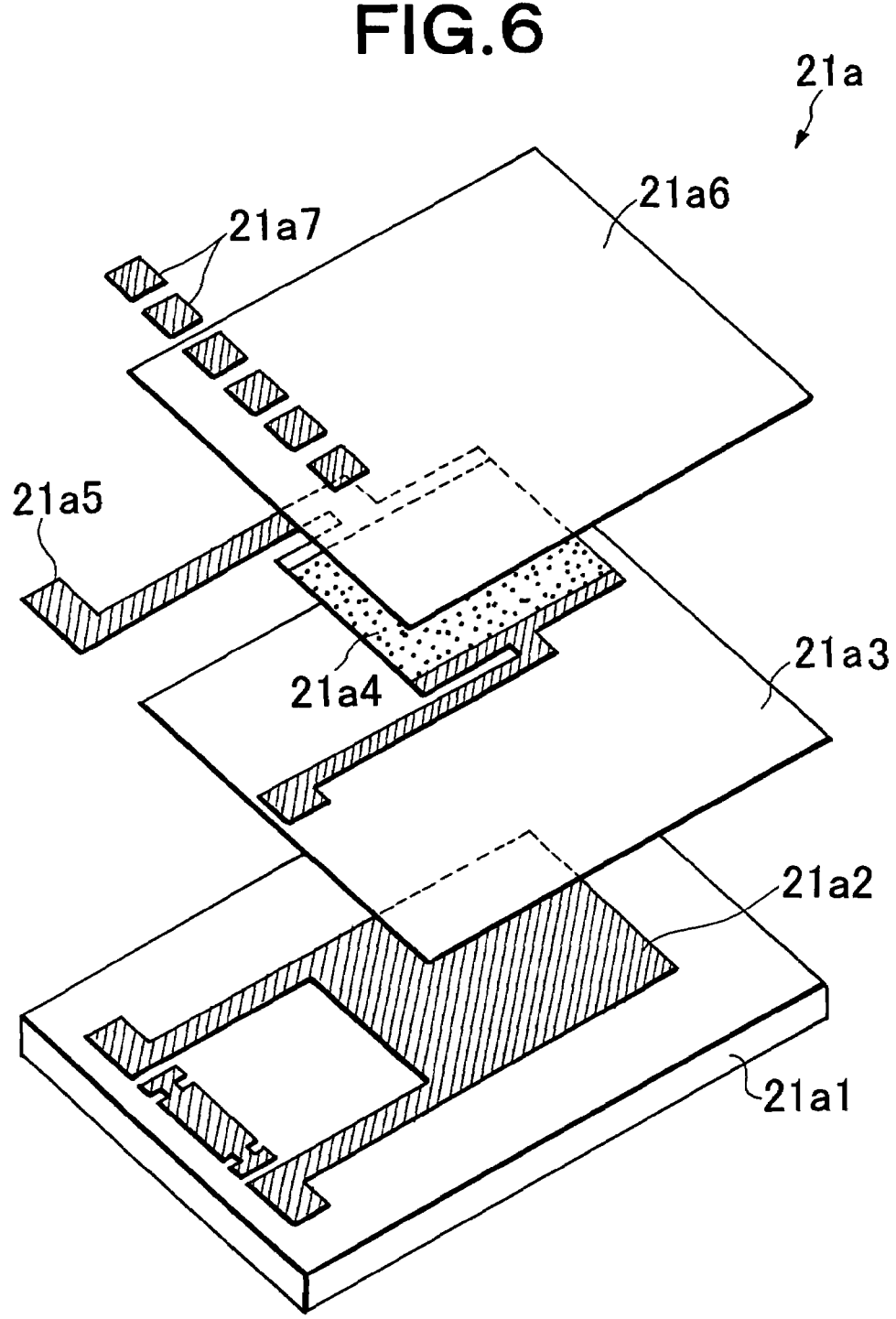
FIG. 6 is an exploded perspective view of a thin film chip of the indirect heating type liquid type detection unit.

FIG. 6 shows an exploded perspective view of the thin film chip 21a of the liquid type detection unit with indirect heating 21. The thin film chip 21a is formed by sequentially laminating a substrate 21a1 made of $Al_2O_3$, a temperature-sensitive body 21a2 made of Ti/Pt, an interlayer insulation film 21a3 made of $SiO_2$, a heating body 21a4 made of $TaSiO_2$ and heating body electrode 21a5 made of Ni, a protection film 21a6 made of $SiO_2$, and an electrode pad 21a7 made of Ti/Au. Although not shown, the temperature-sensitive body 21a2 is formed in a meandering pattern. Although the thin film chip 22a of the liquid temperature detection unit 22 has the same configuration, it does not activate the heating body but only a temperature-sensitive body 22a2.

As shown in FIGS. 3 and 4, the molded resin 23 of the liquid type detection unit with indirect heating 21 and liquid temperature detection unit 22 is attached to the case base plate 2a of the measurement unit 3. A cover member 2d is so fixed on the case base plate 2a as to cover the fin 21c for liquid type detection unit and fin 22c for liquid temperature detection unit, thereby forming an introduction passage 24 of liquid to be measured whose both ends are opened and which sequentially passes through the fin 21c for liquid type detection unit and fin 22c for liquid temperature detection unit to extend in the vertical direction as shown in FIGS. 1 to 3. As shown in FIG. 4, the fixation of the cover member 2d to the case base plate 2a presses a flange portion of the molded resin 23 toward the case base plate 2a, thereby fixing the molded resin 23 to the case base plate 2a.

The above-mentioned case base plate 2a, case cover 2b, cover member 2d, first and second flow passages 4T and 4E are formed of a corrosion-resistant material such as a stainless steel.

Figure 7:
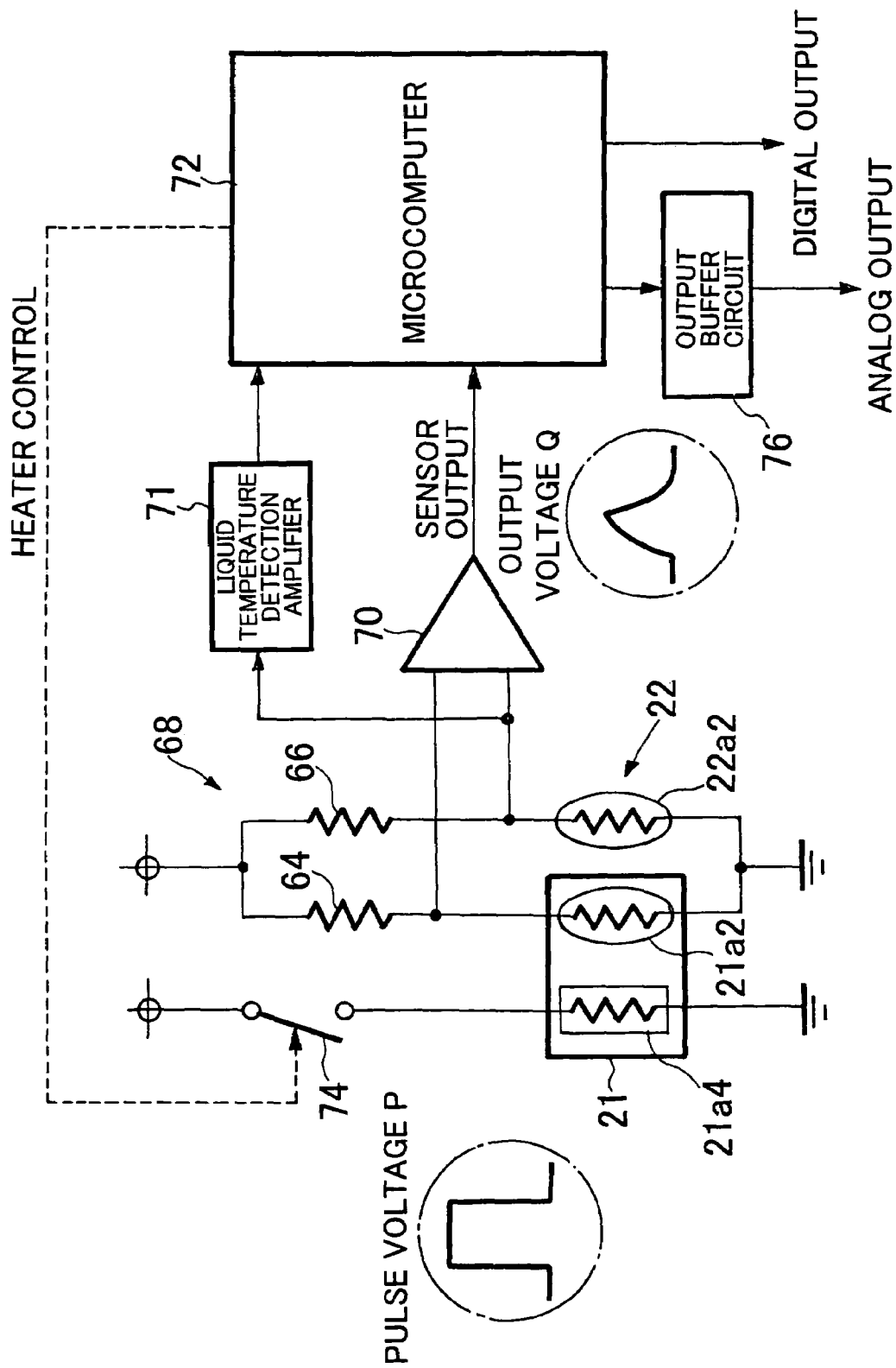
FIG. 7 is a configuration view showing a circuit for liquid type detection.

FIG. 7 shows a configuration of a circuit for liquid type detection in the present embodiment. A bridge circuit 68 is formed by the temperature-sensitive body 21a2 of the liquid type detection unit with indirect heating 21, temperature-sensitive body 22a2 of the liquid temperature detection unit 22, and two resistors 64, 66. An output of the bridge circuit 68 is input to a differential amplifier 70 and then an output (which is referred to as "liquid type detection circuit output" or "sensor output") of the differential amplifier is input to a microcomputer 72 that constitutes an identification calculation unit through a not-shown A/D converter. Further, a liquid temperature-corresponding output value corresponding to the temperature of a liquid to be measured is input to the microcomputer 72 from the temperature-sensitive body 22a2 of the liquid temperature detection unit 22 and through a liquid temperature detection amplifier 71. The microcomputer 72 outputs a heater control signal for controlling opening/closing of a switch 74 located in the current application path to the heating body 21a4 of the liquid type detection unit with indirect heating 21.

A liquid type identification operation will hereinafter be described.

At the liquid type identification operation time, a supply of a liquid to be measured from the tank T to engine E is stopped. That is, the liquid type identification operation is performed in an engine stop state. The supply passage of liquid to be measured starting from the tank T to the engine E, including the internal space of the flow passage 20 of liquid to be measured, first flow passage 4T, and second flow passage 4E of the identification device 1 is always charged with the liquid to be measured. Therefore, at the liquid type identification operation time, the liquid to be measured is not substantially forced to flow through the flow passage 20 of liquid to be measured including the introduction passage 24 of liquid to be measured.

The switch 74 is closed for a predetermined time period (e.g., 3 to 10 seconds; 4 seconds, in FIG. 8) by a heater control signal output from the microcomputer 72 thereto to apply a single pulse voltage P having a predetermined level (e.g., 10 V) to the heating body 21a4, thereby causing the heating body 21a4 to generate heat. An output voltage (sensor output) Q of the differential amplifier 70 at this time gradually increases during application of a voltage to the heating body 21a4 while gradually decreases after the voltage application, as shown in FIG. 8.

Figure 8:
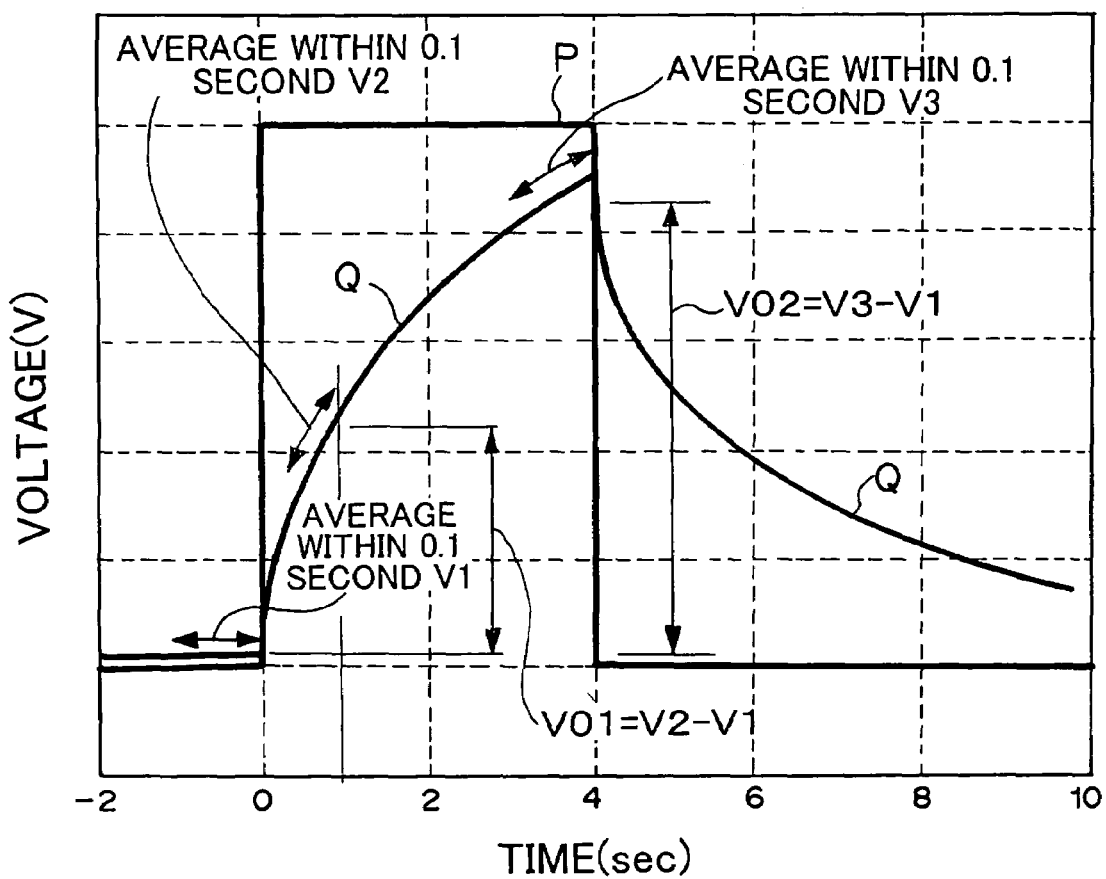
FIG. 8 is a diagram showing a relationship between a single pulse voltage P applied to a heating body and a sensor output Q.

As shown in FIG. 8, the microcomputer 72 samples the sensor output by a predetermined number of times (e.g., 256 times) for a predetermined time period (e.g., 0.1 seconds) before the start of the voltage application to the heating body 21a4 and performs calculation for obtaining the average value of the sensor output to obtain an averaged initial voltage value V1. This averaged initial voltage value V1 corresponds to the initial temperature of the temperature-sensitive body 21a2.

Further, as shown in FIG. 8, the microcomputer 72 samples the sensor output by a predetermined number of times (e.g., 256 times) at a time point when a first time period (e.g., 0.5 to 1.5 seconds which is ½ or less of the single pulse application time; 1 second in FIG. 8), which is comparatively short, has elapsed (to be specific, immediately before the lapse of the first time period) from the start of the voltage application to the heating body and performs calculation for obtaining the average value of the sensor output to obtain an averaged first voltage value V2. This averaged first voltage value V2 corresponds to a first temperature at a time point when the first time period has elapsed from the start of the single pulse application to the temperature-sensitive body 21a2. The microcomputer 72 then computes a difference between the averaged initial voltage value V1 and averaged first voltage value V2 to obtain V01 (=V2−V1) as a liquid-type-corresponding first voltage value.

Further, as shown in FIG. 8, the microcomputer 72 samples the sensor output by a predetermined number of times (e.g., 256 times) at a time point when a second time period (e.g., application time of the single pulse; 4 seconds in FIG. 8), which is comparatively long, has elapsed (to be specific, immediately before the lapse of the second time period) from the start of the voltage application to the heating body and performs calculation for obtaining the average value of the sensor output to obtain an averaged second voltage value V3. This averaged second voltage value V3 corresponds to a second temperature at a time point when the second time period has elapsed from the start of the single pulse application to the temperature-sensitive body 21a2. The microcomputer 72 then computes a difference between the averaged initial voltage value V1 and averaged second voltage value V3 to obtain V02 (=V3−V1) as a liquid-type-corresponding second voltage value.

A part of the heat in the heating body 21a4 which is generated by the single pulse voltage application is transferred to the temperature-sensitive body 21a2 through the liquid to be measured. The heat transfer is mainly divided into two forms which differ depending on the time period that has elapsed from the start of the pulse application. That is, the heat transfer is mainly governed by conduction at a first stage within comparatively a short time period (e.g., 1.5 seconds) from the start of the pulse application; while the heat transfer is mainly governed by natural convection at a second stage starting after the first stage. It is because that, at the second stage, the natural convection is caused by the liquid to be measured which has been heated at the first stage and the ratio of the heat transfer by this natural convection increases.

Figure 9:
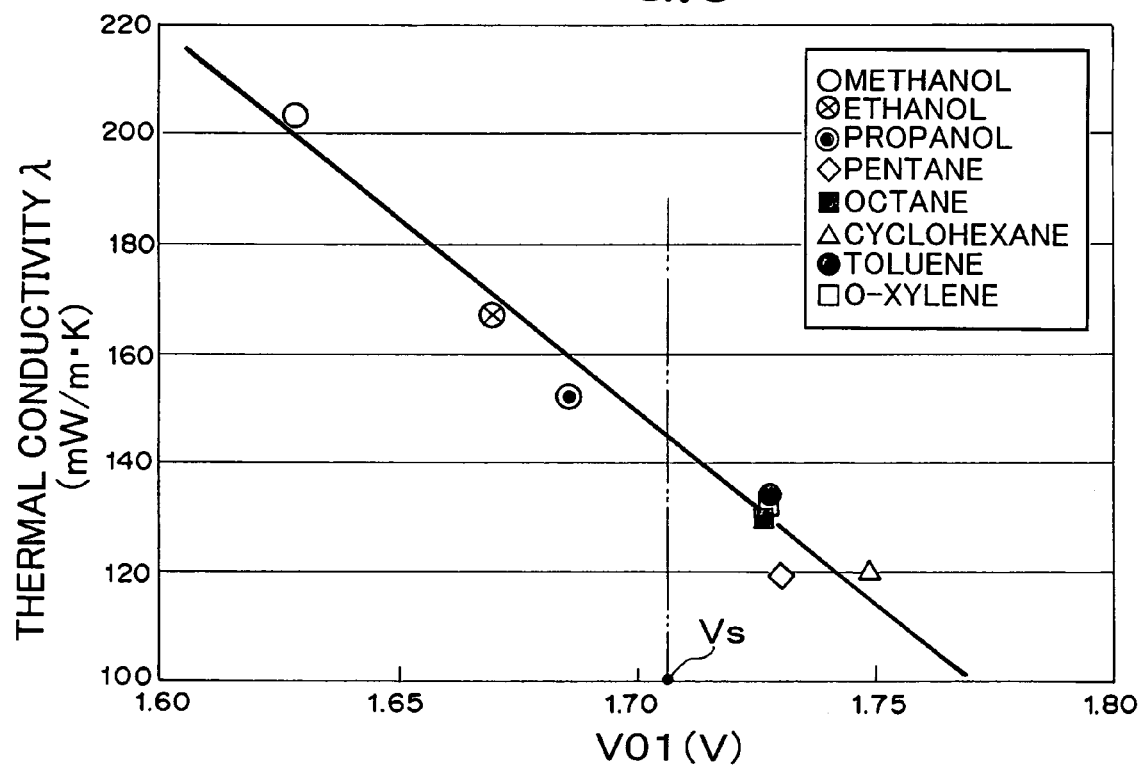
FIG. 9 is a diagram showing a relationship between a liquid-type-corresponding first voltage value V01 and a thermal conductivity of a liquid to be measured.
Figure 10:
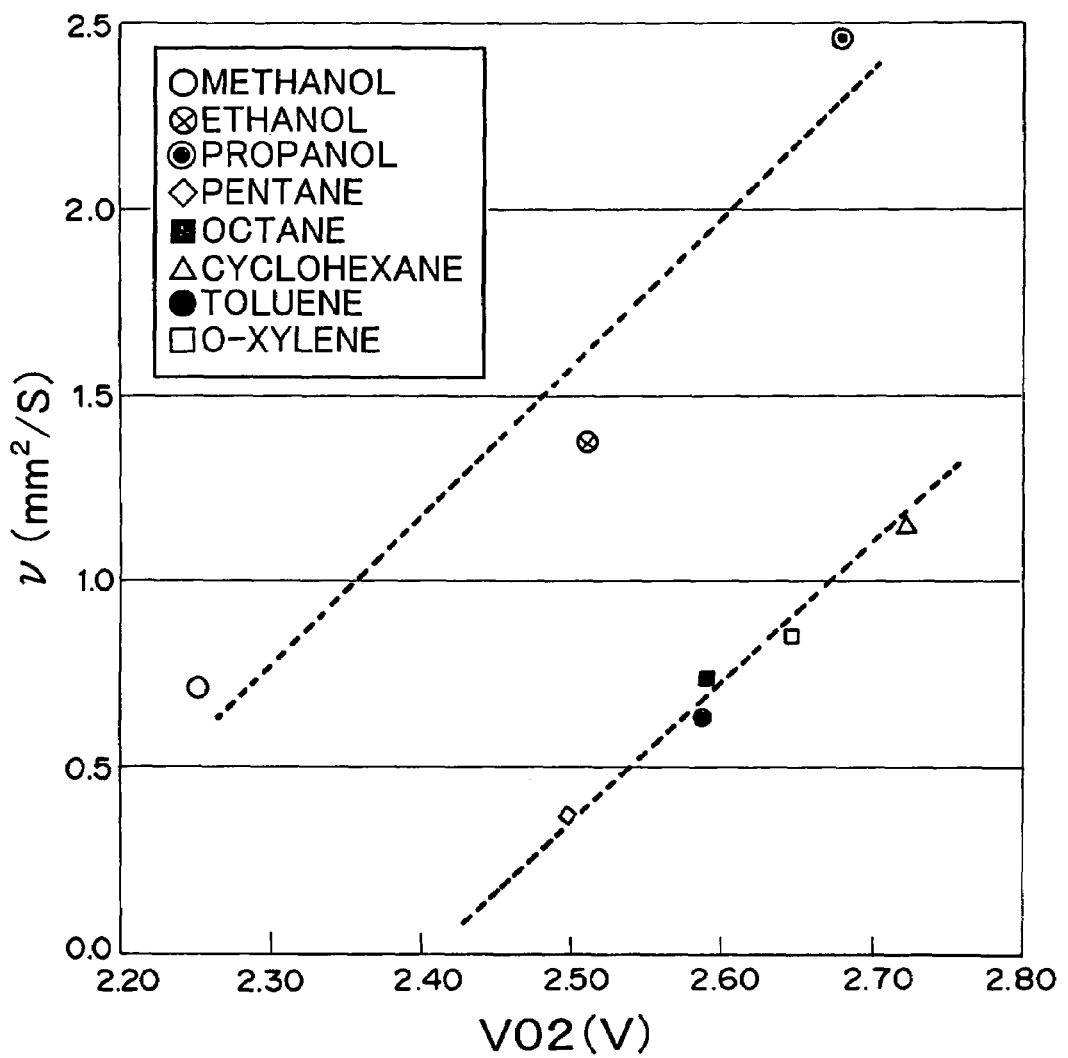
FIG. 10 is a diagram showing a relationship between a liquid-type-corresponding second voltage value V02 and a kinetic viscosity of the liquid to be measured.

A thermal conductivity of the liquid to be measured is greatly involved in the heat transfer at the first stage which is governed by conduction, while a kinetic viscosity of the liquid to be measured is greatly involved in the heat transfer at the second stage which is governed by the natural convection. FIG. 9 shows a relationship between the liquid type-corresponding first voltage values V01 (=V2−V1) and the heat conductivities of some known liquids to be measured (cyclohexane, pentane, octane, toluene, and o-xylene (which are hydrocarbon-based liquids), methanol, ethanol, and propanol (which are alcohol-based liquid)) while setting the first time period to 1.5 seconds in the device according to the present embodiment. Further, FIG. 10 shows a relationship between the liquid-type-corresponding second voltage values V02 (=V3−V1) and the kinetic viscosities of the same liquids as the above while setting the second time period to 5 seconds in the device according to the present embodiment.

As can be seen from FIG. 9, there is a considerable correlation between the liquid-type-corresponding first voltage values V01 thus obtained and heat conductivities of the liquids to be measured. Further, it can be seen that the alcohol-based liquids are located in an area in which the liquid-type-corresponding first voltage values V01 thereof are smaller than a border value Vs and hydrocarbon-based liquids are located in an area in which the values V01 thereof are larger than the border value Vs. Further, as can be seen from FIG. 10, there are considerable correlations respectively between the liquid-type-corresponding second voltage values V02 and kinetic viscosities of the hydrocarbon-based liquids and alcohol-based liquids.

Figure 11:
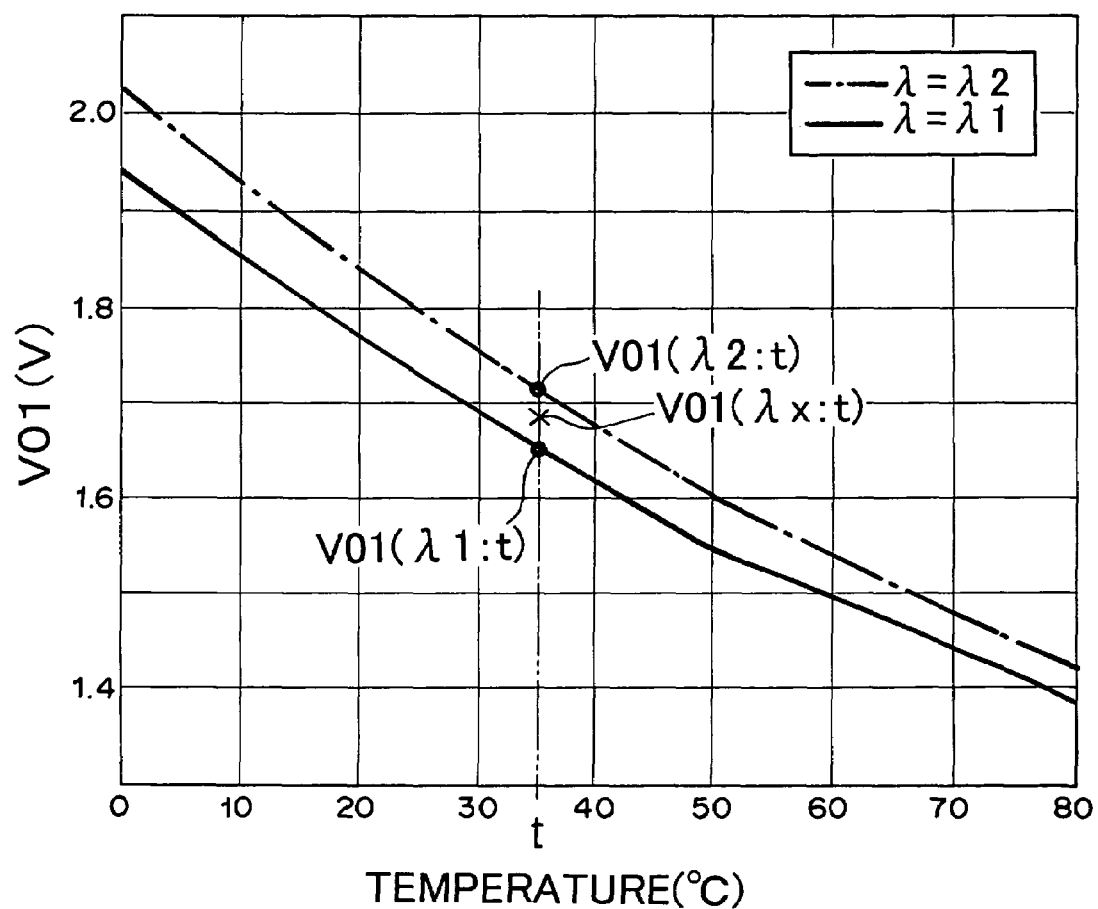
FIG. 11 is a diagram showing an example of a first calibration curve.

In the light of this, in the present embodiment, a first calibration curve indicating a relationship between the temperatures and liquid-type-corresponding first voltage values V01 is previously obtained for some known liquids to be measured (reference liquids to be measured) belonging to the hydrocarbon-based liquid and alcohol-based liquid, and the obtained calibration curve is stored in a storage means of the microcomputer 72. An example of the first calibration curve is shown in FIG. 11. In this example, the first calibration curves are created for the liquids to be measured having a thermal conductivity $\lambda$ of $\lambda 1$ and $\lambda 2$, respectively.

Figure 12:
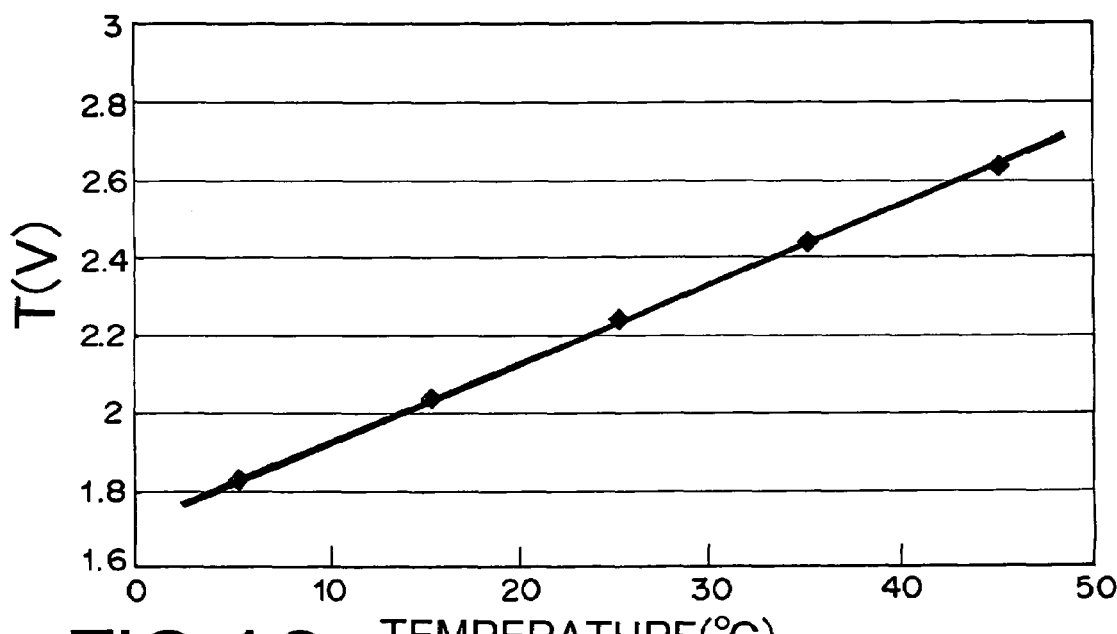
FIG. 12 is a diagram showing an example of a liquid temperature-corresponding output value T.

As shown in FIG. 11, the liquid-type-corresponding first voltage value V01 depends on the temperature. Therefore, when the type (here, the thermal conductivity $\lambda$ is used to identify the type of the liquid to be measured in the identification based on the liquid-type-corresponding first voltage value V01) of the liquid to be measured is identified using the first calibration curve, a liquid temperature-corresponding output value T which is input to the microcomputer 72 from the temperature-sensitive body 22a2 of the liquid temperature detection unit 22 through the liquid temperature detection amplifier 71 is also used. FIG. 12 shows an example of the liquid temperature-corresponding output value T. Such a calibration curve is also stored in the storage means of the microcomputer 72.

In the liquid type measurement, a temperature value is firstly obtained from the liquid temperature-corresponding output value T of the liquid to be measured by using the calibration curve of FIG. 12. Subsequently, with the obtained temperature value set to t, the liquid-type-corresponding first voltage values V01 ($\lambda 1$;t) and V01 ($\lambda 2$;t) of the respective calibration curves corresponding to the temperature value t are obtained based on the first calibration curves of FIG. 11. Then, $\lambda$x of the liquid-type-corresponding first voltage values V01 ($\lambda$x;t) obtained for the liquid to be measured is determined by making proportional calculation using the liquid type-corresponding first voltage values V01 ($\lambda 1$;t), V01 ($\lambda 2$;t) of the respective calibration curves. That is, based on V01 ($\lambda$x;t), V01 ($\lambda 1$;t), and V01 ($\lambda 2$;t), $\lambda$x is obtained using the following equation:

$$\lambda x = \lambda 1 + (\lambda 2 - \lambda 1)[V01(\lambda x;t) - V01(\lambda 1;t)]/[V01(\lambda 2;t) - V01(\lambda 1;t)]$$

As described above, it is possible to accurately and rapidly (in a moment) identify the liquid type. A use of the liquid temperature-corresponding output value T in place of the temperature for obtaining the first calibration curve of FIG. 11 can omit the storage of the calibration curve of FIG. 12 and conversion using the same.

As can be seen from FIG. 9, by determining the high/low relationship between the border value Vs and obtained liquid-type-corresponding first voltage values V01, it is possible to determine whether the liquid to be measured belongs to the hydrocarbon-based liquid or alcohol-based liquid.

Figure 13:
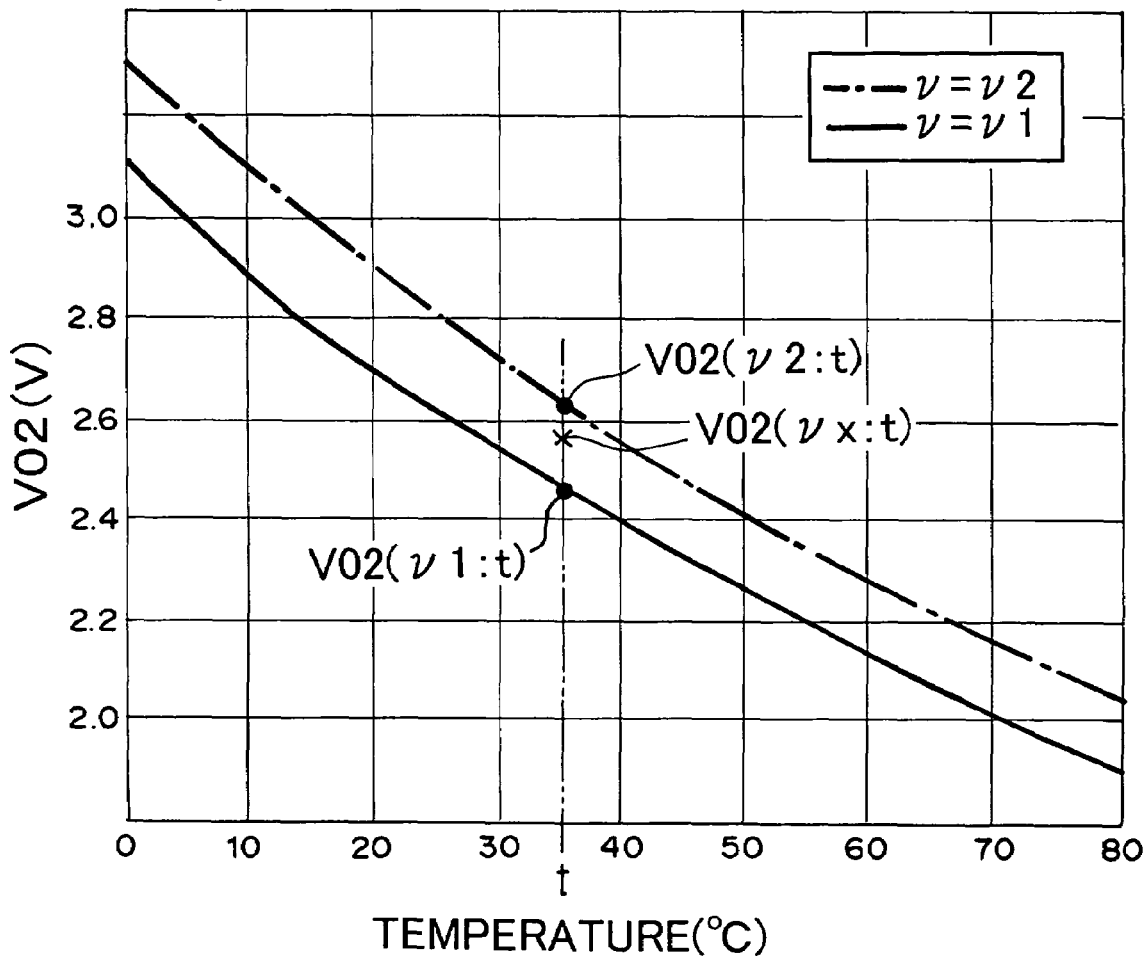
FIG. 13 is a diagram showing an example of a second calibration curve.
Figure 14:
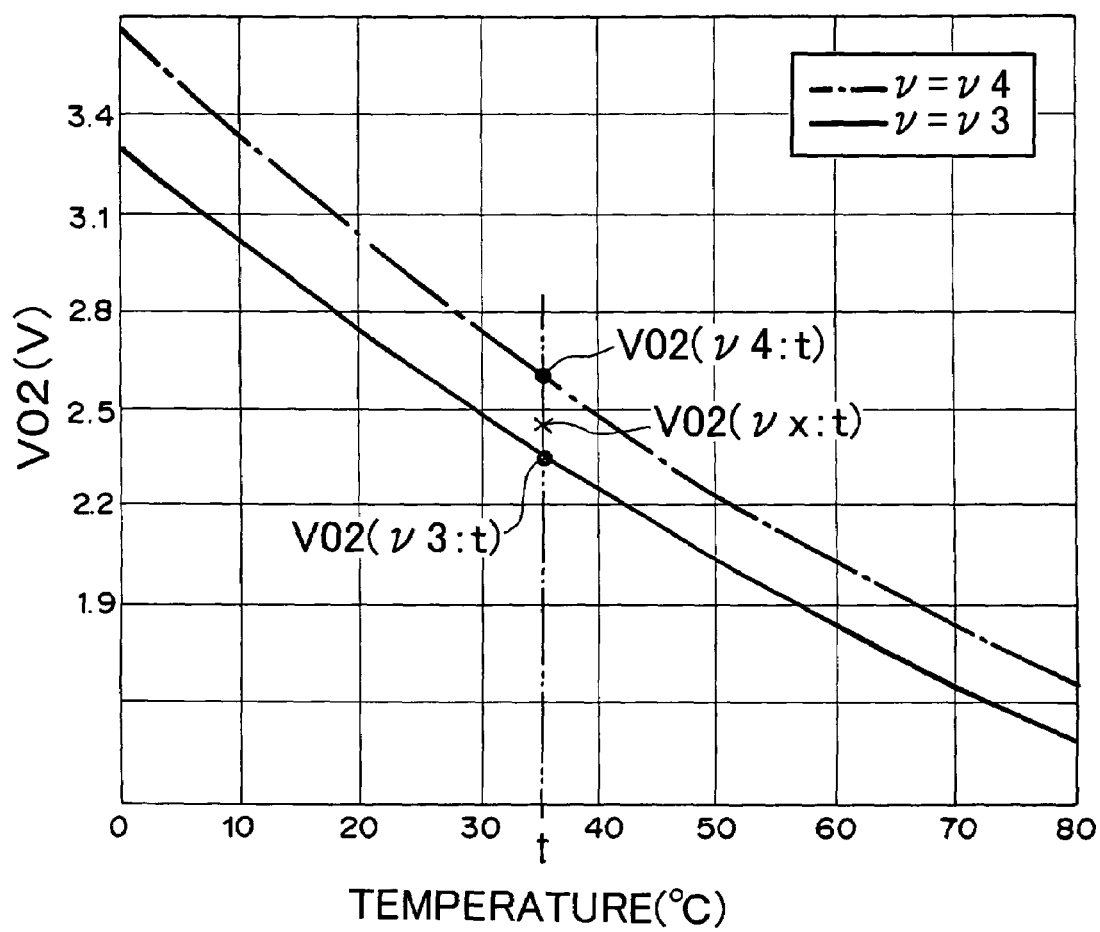
FIG. 14 is a diagram showing another example of the second calibration curve, wherein reference numeral 1 denotes a liquid type identification device, 2 identification sensor unit, 2a case base plate, 2b case cover, 2d cover member, 21 indirect heating type liquid type detection unit, 22 liquid temperature detection unit, 23 molded resin, 24 introduction passage of liquid to be measured, 21a thin film chip, 21b jointing material, 21c, 22c metal fin, 21d bonding wire, 21e,22e external electrode terminal, 21a1 substrate, 21a2,22a2 temperature-sensitive body, 21a3 interlayer insulation film, 21a4 heating body, 21a5 heating body electrode, 21a6 protection film, 21a7 electrode pad, 3 measurement unit, 4T first flow passage, 4E second flow passage, 4T1,4E1 heat insulation cover, 6 housing, 8T,8E pipe joint, 12 circuit board, 13 wiring, 14T tank side potion of flow passage of liquid to be measured, 14E internal-combustion engine side potion of flow passage of liquid to be measured, 20 flow passage of liquid to be measured, 64,66 resistor, 68 bridge circuit, 70 differential amplifier, 71 liquid temperature detection amplifier, 72 microcomputer, 74 switch, 76 output buffer circuit, T tank, and E internal-combustion engine.

Further, in the present embodiment, a second calibration curve indicating a relationship between the temperatures and liquid-type-corresponding second voltage values V02 is previously obtained for some known liquids to be measured (reference liquids to be measured) belonging respectively to the hydrocarbon-based liquid and alcohol-based liquid, and the obtained calibration curve is stored in the storage means of the microcomputer 72. Examples of the second calibration curve are shown in FIGS. 13 and 14. FIG. 13 shows an example of the calibration curve for the hydrocarbon-based liquid, in which the second calibration curves are created for the liquids to be measured having a kinetic viscosity v of v1 and v2, respectively. FIG. 14 shows an example of the calibration curve for the alcohol-based liquid, in which the second calibration curves are created for the liquids to be measured having a kinetic viscosity v of v3 and v4, respectively. That is, in the case where the liquid to be measured is determined to be the hydrocarbon-based liquid in the identification using the liquid-type-corresponding first voltage values V01, the second calibration curve of FIG. 13 is used in the subsequent identification. In the case where the liquid to be measured is determined to be the alcohol-based liquid in the identification using the liquid-type-corresponding first voltage values V01, the second calibration curve of FIG. 14 is used in the subsequent identification.

As shown in FIGS. 13 and 14, the liquid-type-corresponding second voltage values V02 depends on the temperature. Therefore, when the type (here, the kinetic viscosity v is used to identify the type of the liquid to be measured in the identification based on the liquid-type-corresponding second voltage values V02) of the liquid to be measured is identified using the second calibration curve, the liquid temperature-corresponding output value T which is input to the microcomputer 72 from the temperature-sensitive body 22a2 of the liquid temperature detection unit 22 through the liquid temperature detection amplifier 71 is also used.

In the liquid type measurement, a temperature value is firstly obtained from the liquid temperature-corresponding output value T of the liquid to be measured by using the calibration curve of FIG. 12. Subsequently, with the obtained temperature value set to t, the liquid-type-corresponding second voltage values V02 (v1;t) and V02 (v2;t) or V02 (v3;t) and V02 (v4;t) of the respective calibration curves corresponding to the temperature value t are obtained based on the second calibration curves of FIG. 13 or 14. Then, vx of the liquid-type-corresponding second voltage values V02 (vx;t) obtained for the liquid to be measured is determined by making proportional calculation using the liquid-type-corresponding second voltage values V02 (v1;t), V02 (v2;t) or V02 (v3;t), V02 (v4;t) of the respective calibration curves. That is, based on V01 (vx;t), V02 (v1;t), and V02 (v2;t) or (vx;t), V02 (v3;t), and V02 (v4;t), vx is obtained using the following equation:

$$vx=v1+(v2-v1)[V02(vx;t)-V02(v1;t)]/[V02(v2;t)-V02(v1;t)]$$

or $$vx=v3+(v4-v3)[V02(vx;t)-V02(v3;t)]/[V02(v4;t)-V02(v3;t)]$$

As described above, it is possible to accurately and rapidly (in a moment) identify the liquid type. A use of the liquid temperature-corresponding output value T in place of the temperature for obtaining the second calibration curve shown in FIG. 13 or 14 can omit the storage of the calibration curve of FIG. 12 and conversion using the same.

A signal indicating the value (thermal conductivity $\lambda$ or kinetic viscosity $v$) of the liquid type obtained as described above is output to the output buffer circuit 76 shown in FIG. 7 through a not-shown D/A converter. The signal thus input to the output buffer circuit 76 is then output to a main computer (ECU) that performs combustion control and the like of a not-shown car engine as an analog output. An analog output voltage value corresponding to the liquid temperature is also output to the main computer (ECU). Signals indicating the liquid type value and liquid temperature value can be taken as digital output as needed to be input to a device that performs display, alarm, and other operations.

In order to increase the accuracy of the liquid type identification as described above, it is preferable to prevent a forced flow caused by an external factor from occurring as much as possible in the liquid to be measured surrounding the fin 21c for liquid type detection unit and fin 22c for liquid temperature detection unit. In view of this, it is preferable to use the cover member 2d, and in particular, it is preferable to use the cover member 2d to form the introduction passage of liquid to be measured in the vertical direction. The cover member 2d serves also as a protection member for protecting foreign matters from being brought into contact with the internal fins.

In the case where the tilt angle of the measurement unit 3, in particular, the identification sensor unit 2 with respect to the vertical direction is changeable, the cover member 2d exerts the beneficial effect of maintaining the accuracy. That is, in the case where the cover member does not exist, a large change is observed in the form in which the heat generated from the heating body is transferred to the temperature-sensitive body by the natural convection in association with a change in the tilt angle. Accordingly, a change in the liquid-type-corresponding second voltage values V02 of the same liquid to be measured becomes large, with the result that the tilt angle range within which confusion with the output value corresponding to the liquid to be measured of other type does not occur becomes comparatively narrow. On the other hand, in the case where the cover member 2d is provided, a small change is observed in the form in which the heat generated from the heating body is transferred to the temperature-sensitive body by the natural convection in association with a change in the tilt angle (that is, the natural convection mainly occurs along the introduction passage of liquid to be measured in the cover member 2d at all times). Accordingly, a change in the liquid-type-corresponding second voltage values V02 of the same liquid to be measured becomes small, with the result that the tilt angle range within which confusion with the output value corresponding to the liquid to be measured of other type does not occur becomes comparatively wide.

Although a fuel to be supplied to an internal-combustion engine is used as a fluid to be measured in the above embodiment, the hydrocarbon-based liquid and alcohol-based liquid serving as the fluid to be measured in the present invention may be used in other forms. An example of such a form includes a sample for quality control in an oil plant or analysis of a hydrocarbon-based liquid and alcohol-based liquid in the environment. The present invention is also utilized as a device for measuring the thermal conductivity or kinetic viscosity of the hydrocarbon-based liquid and alcohol-based liquid.

What is claimed is:

1. A liquid type identification device which identifies a liquid to be measured belonging to a hydrocarbon-based liquid or an alcohol-based liquid, comprising:

an identification sensor unit which faces a flow passage of the liquid to be measured, the identification sensor unit including a liquid type detection unit with indirect heating which includes a heating body and a temperature-sensitive body and including a liquid temperature detection unit which detects the temperature of the liquid to be measured; and an identification calculation unit which applies a single pulse voltage to the heating body of the liquid type detection unit with indirect heating so as to generate heat and identifies the liquid to be measured according to an output of a liquid type detection circuit formed by the temperature-sensitive body of the liquid type detection unit with indirect heating and the liquid temperature detection unit, wherein the identification calculation unit identifies the liquid to be measured according to a liquid-type-corresponding first voltage value and a liquid-type-corresponding second voltage value, the liquid-type-corresponding first voltage value corresponding to a difference between the initial temperature of the temperature-sensitive body and a first temperature thereof at a time point when a first time period has elapsed from the start of application of the single pulse, the liquid-type-corresponding second voltage value corresponding to a difference between the initial temperature of the temperature-sensitive body and a second temperature thereof at a time point when a second time period longer than the first time period has elapsed from the start of the application of the single pulse.

2. The liquid type identification device as claimed in claim 1, wherein the second time period is the application time of the single pulse.

3. The liquid type identification device as claimed in claim 1, wherein the first time period is ½ or less of the application time of the single pulse.

4. The liquid type identification device as claimed in claim 1, wherein the first time period is 0.5 to 1.5 seconds.

5. The liquid type identification device as claimed in claim 1, wherein the application time of the single pulse is 3 to 10 seconds.

6. The liquid type identification device as claimed in claim 1, wherein an averaged initial voltage value obtained by sampling the initial voltage before the start of the single pulse application to the heating body for a predetermined number of times and averaging the sampled values is used as a voltage value corresponding to the initial temperature of the temperature-sensitive body; an averaged first voltage value obtained by sampling a first voltage at a time point when the first time period has elapsed from the start of the single pulse application to the heating body for a predetermined number of times and averaging the sampled values is used as a voltage value corresponding to the first temperature of the temperature-sensitive body; an averaged second voltage value obtained by sampling a second voltage at a time point when the second time period has elapsed from the start of the single pulse application to the heating body for a predetermined number of times and averaging the sampled values is used as a voltage value corresponding to the second temperature of the temperature-sensitive body; a difference between the averaged first voltage value and averaged initial voltage value is used as the liquid-type-corresponding first voltage value; and a difference between the averaged second voltage value and averaged initial voltage value is used as the liquid-type-corresponding second voltage value.

7. The liquid type identification device as claimed in claim 1, wherein a liquid temperature-corresponding output value corresponding to the temperature of the liquid to be measured is input to the identification calculation unit from the liquid temperature detection unit, and the identification calculation unit uses a calibration curve indicating a relationship between the liquid temperatures and liquid-type-corresponding first voltage values of a plurality of types of known reference liquids to be measured to determine whether the liquid to be measured is the hydrocarbon-based liquid or alcohol-based liquid based on the liquid temperature-corresponding output value and liquid-type-corresponding first voltage value obtained for the liquid to be measured.

8. The liquid type identification device as claimed in claim 7, wherein a liquid temperature-corresponding output value corresponding to the temperature of the liquid to be measured is input to the identification calculation unit from the liquid temperature detection unit, and the identification calculation unit uses a calibration curve which is created respectively for the hydrocarbon-based liquid and alcohol-based liquid and which indicates a relationship between the liquid temperatures and liquid-type-corresponding second voltage values of a plurality of types of known reference liquids to be measured belonging respectively to the hydrocarbon-based liquid and alcohol-based liquid to identify the liquid to be measured based on the liquid temperature-corresponding output value, liquid-type-corresponding second voltage value and the determination result obtained for the liquid to be measured.

9. The liquid type identification device as claimed in claim 1, wherein the identification calculation unit includes a microcomputer.

10. The liquid type identification device as claimed in claim 1, wherein both the liquid type detection unit with indirect heating and liquid temperature detection unit respectively include a heat transfer member for liquid type detection unit and a heat transfer member for liquid temperature detection unit, which are used for heat exchange with the liquid to be measured.

11. A liquid type identifying method, which identifies whether or not a liquid to be measured which is a hydrocarbon-based liquid or an alcohol-based liquid is of a predetermined type by sensing heat generated by energization with a temperature sensor, the identification of whether or not the liquid to be measured is a predetermined hydrocarbon-based liquid or alcohol-based liquid being made based on a combination of a liquid-type-corresponding first voltage value corresponding to a difference between an initial temperature of the temperature sensor and a first temperature thereof obtained at the time point after a first time period has elapsed from a start of the energization and a liquid-type-corresponding second voltage value corresponding to a difference between the initial temperature of the temperature sensor and a second temperature thereof obtained at the time point after a second time period, which is longer than the first time period, has elapsed from the start of the energization.

12. The liquid type identifying method as set forth in claim 11, which identifies whether or not the liquid to be measured is a hydrocarbon-based liquid or an alcohol-based liquid of a predetermined type or with a predetermined solute concentration based on a combination of the liquid-type-corresponding first voltage value and the liquid-type-corresponding second voltage value.

13. The liquid type identifying method as set forth in claim 11, wherein the current is applied by applying a single pulse voltage and the heat generated by the energization is transferred through the liquid to be measured to the temperature sensor disposed to face the liquid.

14. The liquid type identifying method as set forth in claim 11, wherein the predetermined type is gasoline or light oil.

15. The liquid type identifying method as set forth in claim 13, wherein the single pulse voltage is applied to a heater disposed to face the liquid to be measured.

16. The liquid type identifying method as set forth in claim 11, wherein it is determined that the liquid to be measured is a hydrocarbon-based liquid or an alcohol-based liquid having a predetermined specific gravity only when both the liquid-type-corresponding first voltage value and liquid-type-corresponding second voltage value fall within their respective predetermined ranges and, otherwise, it is determined that the liquid to be measured is not a hydrocarbon-based liquid or an alcohol-based liquid having a predetermined specific gravity.

17. The liquid type identifying method as set forth in claim 11, wherein it is determined that the liquid to be measured is gasoline or light oil having a predetermined specific gravity only when both the liquid-type-corresponding first voltage value and liquid-type-corresponding second voltage value fall within their respective predetermined ranges and, otherwise, it is determined that the liquid to be measured is not gasoline or light oil having a predetermined specific gravity.

18. The liquid type identifying method as set forth in claim 16, wherein the predetermined range of the liquid-type-corresponding first voltage value and that of the liquid-type-corresponding second voltage value change depending on a temperature of the liquid to be measured.

19. The liquid type identifying method as set forth in claim 11, wherein the liquid-type-corresponding first voltage value and liquid-type-corresponding second voltage value are obtained based on outputs of a liquid type detecting circuit including both the temperature sensor and a liquid temperature detecting section for detecting a temperature of the liquid to be measured.

20. The liquid type identifying method as set forth in claims 11, wherein an average initial voltage value which is obtained by sampling an initial voltage predetermined number of times before the start of application of the single pulse to the heater and averaging them is used as a voltage value corresponding to the initial temperature of the temperature sensor, an average first voltage value which is obtained by sampling a first voltage at the time after the first time period has elapsed from the start of application of the single pulse to the heater predetermined number of times and averaging them is used as a voltage value corresponding to the first temperature of the temperature sensor, an average second voltage value which is obtained by sampling a second voltage at the time after the second time period has elapsed from the start of application of the single pulse to the heater predetermined number of times and averaging them is used as a voltage value corresponding to the second temperature of the temperature sensor, a difference between the average first voltage value and average initial voltage value is used as the liquid-type-corresponding first voltage value, and a difference between the average second voltage value and average initial voltage value is used as the liquid-type-corresponding second voltage value.

21. The liquid type identifying method as set forth in claims 11, wherein a liquid temperature-corresponding output value corresponding to the temperature of the liquid to be measured is input to the identification calculation unit from the liquid temperature detection unit, and the identification calculation unit uses a calibration curve indicating a relationship between the liquid temperatures and liquid-type-corresponding first voltage values of a plurality of types of known reference liquids to be measured to determine whether the liquid to be measured is the hydrocarbon-based liquid or alcohol-based liquid based on the liquid temperature-corresponding output value and liquid-type-corresponding first voltage value obtained for the liquid to be measured.

22. The liquid type identifying method as set forth in claim 21, wherein a liquid temperature-corresponding output value corresponding to the temperature of the liquid to be measured is input to the identification calculation unit from the liquid temperature detection unit, and the identification calculation unit uses a calibration curve which is created respectively for the hydrocarbon-based liquid and alcohol-based liquid and which indicates a relationship between the liquid temperatures and liquid-type-corresponding second voltage values of a plurality of types of known reference liquids to be measured belonging respectively to the hydrocarbon-based liquid and alcohol-based liquid to identify the liquid to be measured based on the liquid temperature-corresponding output value, liquid-type-corresponding second voltage value and the determination result obtained for the liquid to be measured.

23. The liquid type identifying method as set forth in claims 11, wherein the identification calculation unit includes a microcomputer.

24. The liquid type identifying method as set forth in claim 11, wherein both the liquid type detection unit and liquid temperature detection unit respectively include a heat transfer member for liquid type detection unit and a heat transfer member for liquid temperature detection unit, which are used for heat exchange with the liquid to be measured.

* * * * *